US009694007B2

(12) United States Patent
Woo et al.

(10) Patent No.: US 9,694,007 B2
(45) Date of Patent: Jul. 4, 2017

(54) ORAL COMPLEX COMPOSITION COMPRISING PSEUDOEPHEDRINE AND LEVOCETIRIZINE

(75) Inventors: Jong Soo Woo, Suwon-si (KR); Jae Hyun Park, Suwon-si (KR); Yong Il Kim, Suwon-si (KR); Young Jun Na, Suwon-si (KR); Min Jung Kim, Gunpo-si (KR); Yun Ah Lee, Bucheon-si (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 484 days.

(21) Appl. No.: 13/576,338

(22) PCT Filed: Jan. 18, 2011

(86) PCT No.: PCT/KR2011/000367
§ 371 (c)(1),
(2), (4) Date: Jul. 31, 2012

(87) PCT Pub. No.: WO2011/093612
PCT Pub. Date: Aug. 4, 2011

(65) Prior Publication Data
US 2012/0301548 A1 Nov. 29, 2012

(30) Foreign Application Priority Data
Feb. 1, 2010 (KR) .................. 10-2010-0009314

(51) Int. Cl.
*A61K 9/28* (2006.01)
*A61K 31/495* (2006.01)
*A61K 9/24* (2006.01)
*A61K 31/137* (2006.01)

(52) U.S. Cl.
CPC ............ *A61K 31/495* (2013.01); *A61K 9/209* (2013.01); *A61K 31/137* (2013.01)

(58) Field of Classification Search
CPC ........ A61K 9/28; A61K 9/2806; A61K 9/284; A61K 9/2846; A61K 9/2853; A61K 9/286; A61K 9/2866
USPC ................................................ 424/474–483
See application file for complete search history.

(56) References Cited

U.S. PATENT DOCUMENTS

| 5,681,582 | A | 10/1997 | Gilis et al. |
| 6,171,618 | B1 | 1/2001 | Johnson et al. |
| 6,537,573 | B2 * | 3/2003 | Johnson et al. ............... 424/472 |
| 2004/0121015 | A1 * | 6/2004 | Chidlaw et al. .............. 424/471 |
| 2004/0170690 | A1 * | 9/2004 | Fanara ................... A61K 9/209 424/472 |
| 2005/0095288 | A1 * | 5/2005 | Honea ................... A61K 9/209 424/464 |
| 2006/0034928 | A1 | 2/2006 | Fanara et al. |
| 2007/0218140 | A1 | 9/2007 | Tanabe et al. |
| 2009/0074866 | A1 * | 3/2009 | Chen ............................. 424/481 |
| 2010/0003289 | A1 | 1/2010 | Woo et al. |

FOREIGN PATENT DOCUMENTS

| CN | 1500487 A | 6/2004 |
| CN | 1520285 A | 8/2004 |
| CN | 1265793 C | 7/2006 |
| CN | 100490809 C | 5/2009 |
| JP | 2005306778 A | 11/2005 |
| JP | 2007191474 A | 8/2007 |
| KR | 10-2004-0005257 A | 1/2004 |
| KR | 10-2006-0113016 A | 11/2006 |
| WO | 2008/008434 A1 | 1/2008 |

OTHER PUBLICATIONS

International Searching Authority, International Search Report for PCT/KR2011/000367 dated Sep. 21, 2011.
J.P. Tillement et al.,"Compared Pharmacological Characteristics in humans of racemic cetrizine and levocetrizine, two histamine H1-receptor antagonists", Biochemical Pharmacology, 2003, vol. 66, Abstract.
Chinese Patent Office, Chinese Office Action issued in corresponding CN Application No. 201180007804.9, dated Jun. 9, 2013.
Japan Patent Office, Communication dated Dec. 2, 2014, issued in corresponding Japanese application No. 2012-551906.

* cited by examiner

*Primary Examiner* — Micah-Paul Young
(74) *Attorney, Agent, or Firm* — Sughrue Mion, PLLC

(57) ABSTRACT

An oral complex composition which comprises (i) a core comprising a swellable hydrogel-forming agent and pseudoephedrine, or a pharmaceutically acceptable salt thereof; (ii) a first coating layer encasing the core which comprises a water-soluble substance; and (iii) a second coating layer deposited on the first coating layer which comprises levocetirizine or a pharmaceutically acceptable salt thereof together with polyvinylalcohol, povidone, polyvinylalcohol-polyethyleneglycol graft copolymer or a mixture thereof, has an improved levocetirizine releasing rate and does not show a delayed release behavior even after a long storage period. Accordingly, the inventive oral complex composition is useful for treating perennial or seasonal allergic diseases including nasal obstruction, sneezing, and rhinorrhea.

5 Claims, 9 Drawing Sheets

ORAL COMPLEX COMPOSITION COMPRISING PSEUDOEPHEDRINE AND LEVOCETIRIZINE

FIELD OF THE INVENTION

The present invention relates to an oral complex composition comprising pseudoephedrine and levocetirizine, which exhibits an improved levocetirizine releasing rate and does not show a delayed release behavior even after a long period of storage.

BACKGROUND OF THE INVENTION

Pseudoephedrine has been used in combination with cetirizine for treating perennial or seasonal allergic diseases including nasal obstruction, sneezing, and rhinorrhea. Commercially available complex formulations are ZYRTEC PLUS (UCB Pharma) and KOSSAK (Hanmi Pharm Co. Ltd), in which the pseudoephedrine shows a sustained release rate over 10 to 12 hours while the cetirizine shows a fast release within 2 hours.

The pseudoephedrine has an in vivo ranging from 5 to 7 hours and is orally administered 3 or 4 times/day in divided doses. Therefore, the pseudoephedrine must be prepared in the form of a sustained release formulation when used in combination with a single dose drug such as cetirizine for the sake of the patient's convenience.

Various complex compositions comprising pseudoephedrine and cetirizine have been developed. For example, Korean Patent Pub. No. 2009-26140 discloses a bi-layer tablet composed of a pseudoephedrine segment which contains pseudoephedrine and hydroxypropylmethylcellulose (HPMC) and a cetirizine segment containing cetirizine, lactose, and microcrystalline cellulose. However, the bi-layer tablet can not be prepared using a conventional monolayer tablet machine, but the use of a special tablet press machine which is capable of pressing each of granular forms of the drugs into a bi-layer tablet is required.

Further, Korean Patent Pub. No. 2006-2235 discloses a sustained-release formulation which is prepared by a method comprising the steps of: coating white sugar with pseudoephedrine HCl; coating the pseudoephedrine HCl-coated white sugar with ethylcellulose which is a coating layer-forming agent for controlling sustained release of the pseudoephedrine to obtain a sustained release core; and coating the sustained release core with pseudoephedrine and cetirizine. This formulation is composed of a part that enables both a fast release and a sustained release of pseudoephedrine and the part that allows a fast release of cetirizine.

Levocetirizine, an isomer of cetirizine, is a histamine H1 receptor antagonist, and it is used as an antihistamine agent, which is marketed in Korea under the trade name of XYZAL™ (UCB pharma), which is a fast release drug formulation having a releasing rate of 80% or more within 30 min. Levocetirizine is also used in combination with pseudoephedrine for treating perennial or seasonal allergic diseases including nasal obstruction, sneezing, and rhinorrhea.

However, there has been a need for developing a pseudoephedrine-levocetirizine containing complex composition which has an improved levocetirizine releasing rate and does not show a delayed release behavior even after a long storage time.

SUMMARY OF THE INVENTION

Accordingly, it is an object of the present invention to provide an oral complex composition comprising pseudoephedrine and levocetirizine, which has an improved levocetirizine releasing rate and does not show a delayed release behavior even after a long storage time.

In accordance with an aspect of the present invention, there is provided an oral complex composition comprising:

(i) a core comprising a swellable hydrogel-forming agent and pseudoephedrine, or a pharmaceutically acceptable salt thereof;

(ii) a first coating layer which encases the core and comprises a water-soluble substance; and (iii) a second coating layer deposited on the first coating layer, which comprises levocetirizine or a pharmaceutically acceptable salt thereof together with polyvinylalcohol, povidone, polyvinylalcohol-polyethyleneglycol graft copolymer or a mixture thereof.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Figure 1:
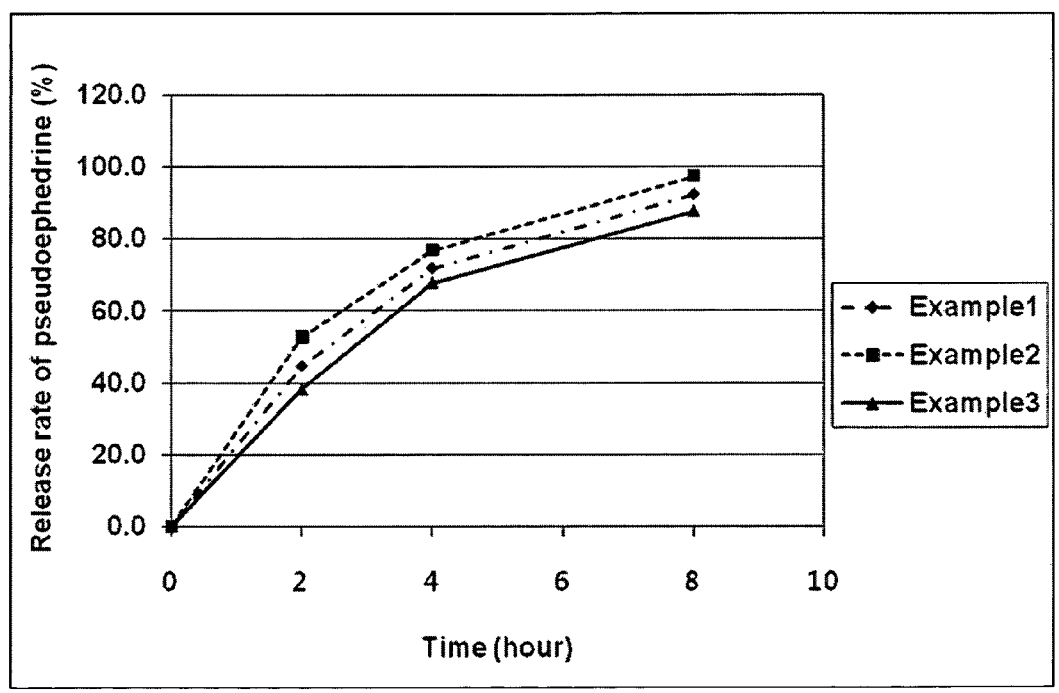
FIG. 1: the release rates of pseudoephedrine from the complex compositions obtained in Examples 1 to 3.

Hereinafter, a detailed description of the present invention is given.

In a conventional complex composition, a levocetirizine-containing coating layer is directly formed on a pseudoephedrine-containing core. Therefore, when the complex composition absorbs water, a swellable hydrogel forming agent included in the core swells to encase the levocetirizine-containing coating layer, and the levocetirizine which is not released, converts into a hydrogel. As a result, the release behavior of levocetirizine from the coating layer is delayed.

The present inventors have therefore endeavored to develop a novel complex composition and have found that an water-soluble coating layer formed between the pseudoephedrine-containing core and the levocetirizine-containing coating layer inhibits a delayed release behavior of levocetirizine which is caused by the hydrogel, and the levocetirizine-containing coating layer which is formed using levocetirizine together with polyvinylalcohol, povidone, polyvinylalcohol-polyethyleneglycol graft copolymer or a mixture thereof, minimerizes the delayed release for a storage time, thereby the complex composition shows the levocetirizine releasing rate of 80% or more within 30 min and does not show a delayed release behavior even after 6 month-storage at 40° C. and a relative humidity (RH) of 75%.

The inventive complex composition is characterized by comprising (i) a sustained release core of pseudoephedrine, which comprises a swellable hydrogel-forming agent and pseudoephedrine, or a pharmaceutically acceptable salt thereof; (ii) a first coating layer which encases the core and comprises a water-soluble substance; and (iii) a second coating layer deposited on the first coating layer, which comprises levocetirizine or a pharmaceutically acceptable salt thereof together with polyvinylalcohol, povidone, polyvinylalcohol-polyethyleneglycol graft copolymer or a mixture thereof to allow a fast release of levocetirizine.

(a) Active Ingredient

The active ingredient comprises pseudoephedrine or a pharmaceutically acceptable salt thereof; and levocetirizine or a pharmaceutically acceptable salt thereof. The pseudoephedrine is included in the core and the levocetirizine is included in the coating layer. All of them are useful for treating perennial or seasonal allergic diseases including nasal obstruction, sneezing, and rhinorrhea.

Based on a unit dosage, the pseudoephedrine or the pharmaceutically acceptable salt thereof is administrated in an amount ranging from about 30 mg to about 240 mg and the levocetirizine or a pharmaceutically acceptable salt thereof is administrated in an amount ranging from about 1 mg to about 10 mg.

(b) Swellable Hydrogel Forming Agent

The swellable hydrogel forming agent is an excipient for a sustained release of pseudoephedrine. During release or in vivo, the swellable hydrogel forming agent absorbs water to be a gel. Examples for the swellable hydrogel forming agent include polyoxyethylene, methylcellulose, hydroxypropylcellulose, hydroxypropylmethylcellulose, carboxymethylcellulose or its salt, carbomer, a qum (e.g., xanthan gum, locust bean gum, and guar gum), alginic acid or its salt (e.g., propyleneglycol alginate and sodium alginate), and a mixture thereof, preferably polyoxyethylene.

The swellable hydrogel forming agent is used in an amount ranging from 0.1 to 10 weight part, based on 1 weight part of pseudoephedrine.

The core may further comprise a pharmaceutically acceptable additive with the swellable hydrogel forming agent, and pseudoephedrine or a pharmaceutically acceptable salt thereof (c) Water-soluble Substance as a Material for Forming the First Coating Layer The water-soluble substance is a material which can be swelled with the swellable hydrogel forming agent in the core. It inhibits a delayed release behavior of levocetirizine caused by the hydrogel in the second coating layer, but has no effect on the releasing rate of pseudoephedrine from the core.

Examples for the water-soluble substance include hydroxypropylcellulose, hydroxypropylmethylcellulose, and a mixture thereof.

The first coating layer may further comprise a pharmaceutically acceptable additive as well as the water-soluble substance.

The inventive complex composition comprises the first coating layer in an amount of 17 percent by weight part or less, preferably 1 to 17 percent by weight part based on the core. When the amount of the first coating layer is over 17 percent by weight part, the release behavior of the pseudoephedrine from the core is changed significantly.

(d) Material for Forming the Second Coating Layer

The second coating layer forming material forms the second coating layer with levocetirizine, and examples for the material include polyvinylalcohol, povidone, polyvinylalcohol-polyethyleneglycol graft copolymer and a mixture thereof.

The material allows a fast release of levocetirizine and inhibits a delayed release behavior of levocetirizine during the storage.

The material is used in an amount ranging from 10 to 100 weight part based on 1 weight part of levocetirizine.

The second coating layer may further comprise a pharmaceutically acceptable additive together with the second coating layer forming material, and levocetirizine or a pharmaceutically acceptable salt thereof.

The inventive complex composition comprises the second coating layer in an amount of 5 to 50 percent by weight part based on the core.

Examples for the pharmaceutically acceptable additive include disintegrating agent, diluent, stabilizer, binder, lubricant and a mixture thereof, and an amount of the additive used may be controlled properly.

The inventive complex composition may be formulated in accordance with any of conventional methods in the form of a coated tablet for oral administration.

Specifically, the inventive complex composition may be formulated by a method comprising the steps of (1) subjecting a mixture of a swellable hydrogel forming agent, pseudoephedrine or a pharmaceutically acceptable salt thereof, and optionally a pharmaceutically acceptable additive to a tablet compression to form a sustained-release core, (2) conducting a first coating to the core using a coating solution which is prepared by dissolving a water-soluble substance and optionally a pharmaceutically acceptable additive in a solvent (e.g. a mixture of acetone and water) to form a first coating layer on the core, (3) carrying out a second coating to the core having the first coating layer, using a second solution which is prepared by dissolving a second coating layer forming material, levocetirizine or a pharmaceutically acceptable salt thereof, and optionally a pharmaceutically acceptable additive in a solvent (e.g. a mixture of acetone and water) to form a second coating layer on the first coating layer.

The inventive oral complex composition showed a levocetirizine releasing rate of 80% or more in a 0.1N HCl solution within 30 min in the releasing test, and no delayed release behavior of levocetirizine was observed in the condition of 40° C. and a relative humidity (RH) of 75% after 6 months in storage. Accordingly, the inventive oral complex composition is useful for treating perennial and seasonal allergic diseases including nasal obstruction, sneezing and rhinorrhea.

The following Examples are intended to further illustrate the present invention without limiting its scope.

EXAMPLES 1 to 3

Preparation of Sustained-release Pseudoephedrine Tablet (Sustained-release Core)

In accordace with the composition (unit: mg) as shown in Table 1, pseudoephedrine HCl (Cheng Fong Chemincal, Taiwan), polyoxyethylene (Dow chemical, US) as a swellable hydrogel forming agent, hydroxypropylmethylcellulose (Shinetsu, JP), xanthan gum (ISP, US), and a additive comprising Ludipress (Ludipress; BASF, Germany), Light anhydrous silicic acid (Degussa), butylated hydroxy toluene (BHT; UENO Fine chemical, US) and magnesium stearate were mixed and formulated to a sustained-release tablet (Sustained-release core) comprising pseudoephedrine using tablet machine (MRC-45, Sejong Pharmatech Co. Ltd., KR).

TABLE 1

| Component | Example 1 | Example 2 | Example 3 |
|---|---|---|---|
| Pseudoephedrine HCl core | 120.0 | 120.0 | 120.0 |
| Polyoxyethylene | 160.0 | — | — |
| Hydroxypropylmethyl cellulose | — | 120.0 | — |
| Xanthan gum | — | — | 80.0 |
| Ludipress | 300.0 | 300.0 | 300.0 |
| Light anhydrous silicic acid | 10.0 | 10.0 | 10.0 |
| BHT | 0.3 | 0.3 | 0.3 |
| Magnesium stearate | 10.0 | 10.0 | 10.0 |
| total | 600.3 | 560.3 | 520.3 |

EXAMPLES 4 to 8

Preparation of the Inventive Complex Composition (1)

A first and second coating solution were prepared in accordance with the composition as shown in Table 2 and coated on the core of the sustained-release pseudoephedrine tablet obtained in Example 1 successively to obtain a complex composition.

Specifically, hydroxypropylmethylcellulose (Shinetsu, JP), acetylated monoglyceride (Myvacet; Kerry bio-science, US), and talc were dissolved in a mixture of acetone and water to obtain the first coating solution. The core was coated with the first coating solution using a coater (SFC-30C, Sejong Pharmatech) and dried to form a first coating layer thereon. Polyvinylalcohol (Kurai, JP), hydroxypropylcellulose (Nisso chemical, JP) and levocetirizine HCl were dissolved in a mixture of acetone and water to obtain a second coating solution. The core having the first coating layer was coated with the second coating solution using a coater and dried to form a complex composition having a second coating layer on the first coating layer. For coating process, a supply air temperature and a product temperature were set at 50° C. and 30° C. respectively. After the coating process, the drying process was carried out for 30 min to remove residual acetone and water.

COMPARATIVE EXAMPLES 1 to 3

Preparation of Conventional Complex Composition

A conventional complex composition was prepared in the same manner as in Example 4 except forming a levocetirizine coating layer using a coating solution prepared according to the composition as shown in Table 3, without forming the aqueous first coating layer.

TABLE 3

| Component | Comparative Example 1 | Comparative Example 2 | Comparative Example 3 |
|---|---|---|---|
| Pseudoephedrine core | Example 1 600 | Example 2 560 | Example 3 520 |
| Hydroxypropylmethyl-cellulose | 40 | 40 | 40 |
| Myvacet | 8 | 8 | 8 |
| Talc | 2 | 2 | 2 |
| Levocetirizine HCl | 2.5 | 2.5 | 2.5 |
| <Water> | <200> | <200> | <200> |
| <Acetone> | <200> | <200> | <200> |
| Total amount of tablet | 652.5 | 612.8 | 572.8 |

EXAMPLES 9 and 10

Preparation of the Inventive Complex Composition (2)

Desired compositions were prepared in the same manner as in Example 4 using the sustained-release pseudoephedrine tablet obtained in Examples 2 and 3 as a core and the composition prepared according to the composition as shown in Table 4.

TABLE 4

| | Component | Example 9 | Example 10 |
|---|---|---|---|
| First coating solution | Pseudoephedrine core | Example 2 560.0 | Example 3 520.0 |
| | Hydroxypropylmethylcellulose | 5.0 | 5.0 |
| | Myvacet | 1.0 | 1.0 |
| | Talc | 0.25 | 0.25 |
| | <Acetone> | <50> | <50> |
| | <Water> | <25> | <25> |

TABLE 2

| | Component | Example 4 | Example 5 | Example 6 | Example 7 | Example 8 |
|---|---|---|---|---|---|---|
| First coating solution | Pseudoephedrine core | Example 1 600.0 | Example 1 600.0 | Example 1 600.0 | Example 1 600.0 | Example 1 600.0 |
| | Hydroxypropylmethyl cellulose | 2.5 | 5.0 | 20.0 | 80.0 | 160.0 |
| | Myvacet | 0.5 | 1.0 | 4.0 | 16.0 | 32.0 |
| | Talc | 0.15 | 0.25 | 1.0 | 4.0 | 8.0 |
| | <Acetone> | <50> | <50> | <200> | <800> | <1600> |
| | <Water> | <25> | <25> | <100> | <400> | <800> |
| Second coating solution | Polyvinylalcohol | 37.0 | 37.0 | 37.0 | 37.0 | 37.0 |
| | Hydroxypropyl cellulose | 3.0 | 3.0 | 3.0 | 3.0 | 3.0 |
| | Levocetirizine HCl | 2.5 | 2.5 | 2.5 | 2.5 | 2.5 |
| | <Water> | <400> | <400> | <400> | <400> | <400> |
| | <Acetone> | <40> | <40> | <40> | <40> | <40> |
| Total amount of tablet | | 645.65 | 648.75 | 667.50 | 742.50 | 842.50 |
| The content of the first coating layer to the core (wt %) | | 0.5% | 1.0% | 4.2% | 16.7% | 33.3% |

TABLE 4-continued

| | Component | Example 9 | Example 10 |
|---|---|---|---|
| Second coating solution | Polyvinylalcohol | 37.0 | 37.0 |
| | Hydroxypropylcellulose | 3.0 | 3.0 |
| | Levocetirizine HCl | 2.5 | 2.5 |
| | <Water> | <400> | <400> |
| | <Acetone> | <40> | <40> |
| | Total amount of tablet | 609.05 | 569.05 |

EXAMPLES 11 to 13

Preparation of the Inventive Complex Composition (3)

Desired compositions were prepared in the same manner as in Example 4 using the sustained-release pseudoephedrine tablet obtained in Example 1 as a core and the composition prepared according to the composition as shown in Table 5. Povidone (BASF, Germany) and PVA-PEG graft copolymer (Kollicoat IR, BASF, Germany) were used as a material for forming the second coating layer.

TABLE 5

| | Component | Example 11 | Example 12 | Example 13 |
|---|---|---|---|---|
| First coating solution | Pseudoephedrine core | Example 1 600.0 | Example 1 600.0 | Example 1 600.0 |
| | Hydroxypropylmethyl-cellulose | 5.0 | 5.0 | 5.0 |
| | Myvacet | 1.0 | 1.0 | 1.0 |
| | Talc | 0.3 | 0.3 | 0.3 |
| | <Water> | <50> | <50> | <50> |
| | <Acetone> | <25> | <25> | <25> |
| Second coating solution | Povidone | 37.0 | — | 10.0 |
| | PVA-PEG graft copolymer | — | 37.0 | 27.0 |
| | Hydroxypropylcellulose | 3.0 | 3.0 | 3.0 |
| | Levocetirizine HCl | 2.5 | 2.5 | 2.5 |
| | <Water> | <400> | <400> | <400> |
| | <Acetone> | <40> | <40> | <40> |
| | Total amount of tablet | 648.75 | 648.75 | 648.75 |

COMPARATIVE EXAMPLE 4

Preparation of Comparative Complex Composition

Desired compositions were prepared in the same manner as in Example 4 using the sustained-release pseudoephedrine tablet obtained in Example 1 as a core and the composition prepared according to the composition as shown in Table 6. Hydroxypropylmethylcellulose was used as a material for forming the second coating layer

TABLE 6

| | Component | Comparative Example 4 |
|---|---|---|
| First coating solution | Pseudoephedrine core | Example 1 600 |
| | Hydroxypropylmethylcellulose | 5.0 |
| | Myvacet | 1.0 |
| | Talc | 0.25 |
| | <Acetone> | <50> |
| | <Water> | <25> |

TABLE 6-continued

| | Component | Comparative Example 4 |
|---|---|---|
| Second coating solution | Hydroxypropylmethylcellulose | 40 |
| | Myvacet | 8 |
| | Talc | 2 |
| | Levocetirizine HCl | 2.5 |
| | <Acetone> | <400> |
| | <Water> | <200> |
| | Total amount of tablet | 658.75 |

EXPERIMENTAL EXAMPLE 1

Releasing Test of the Sustained-release Pseudoephedrine Tablet

The sustained-release pseudoephedrine tablets obtained in Examples 1 to 3 were subjected to a releasing test in 900 ml of 0.1N HCl solution at a rate of 50 rpm according to the paddle method (the releasing method type II described in the Korean pharmacopoeia). Further, the releasing test was conducted to the cores having the first coating layer which are obtained before the process for forming the second coating layer in Examples 4 to 8.

Figure 2:
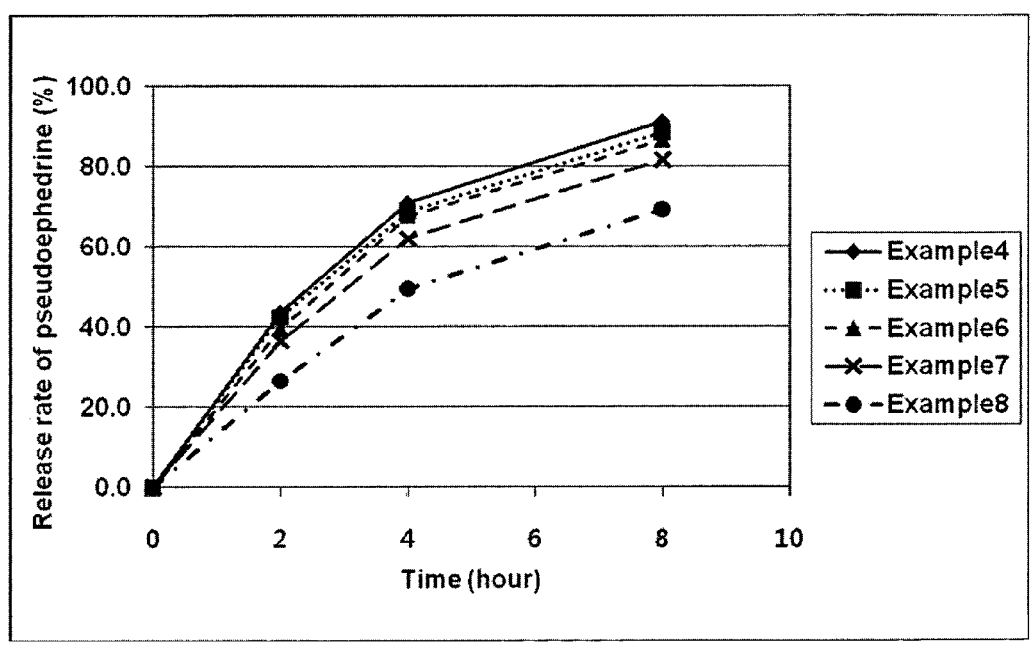
FIG. 2: the release rates of pseudoephedrine from the complex compositions obtained in Examples 4 to 8.

The effluent was collected at 2 hr, 4 hr, and 8 hr after releasing and the releasing rate of pseudoephedrine was calculated using the effluent. The results are shown in FIGS. 1 and 2. And a similarity factor (f2) of the pseudoephedrine release behavior in Examples 1, and 4 to 8 was calculated and the result is shown in FIG. 3.

Figure 3:
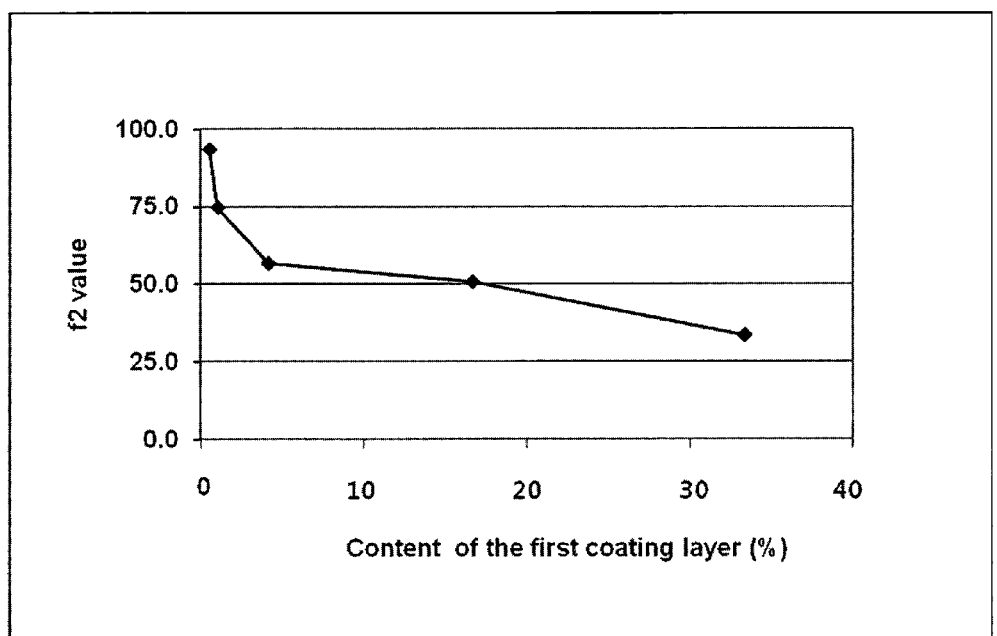
FIG. 3: the similarity factor (f2) of the pseudoephedrine release behaviors depending on the amount of the first coating layer in the complex compositions obtained in Examples 4 to 8.
Figure 4:
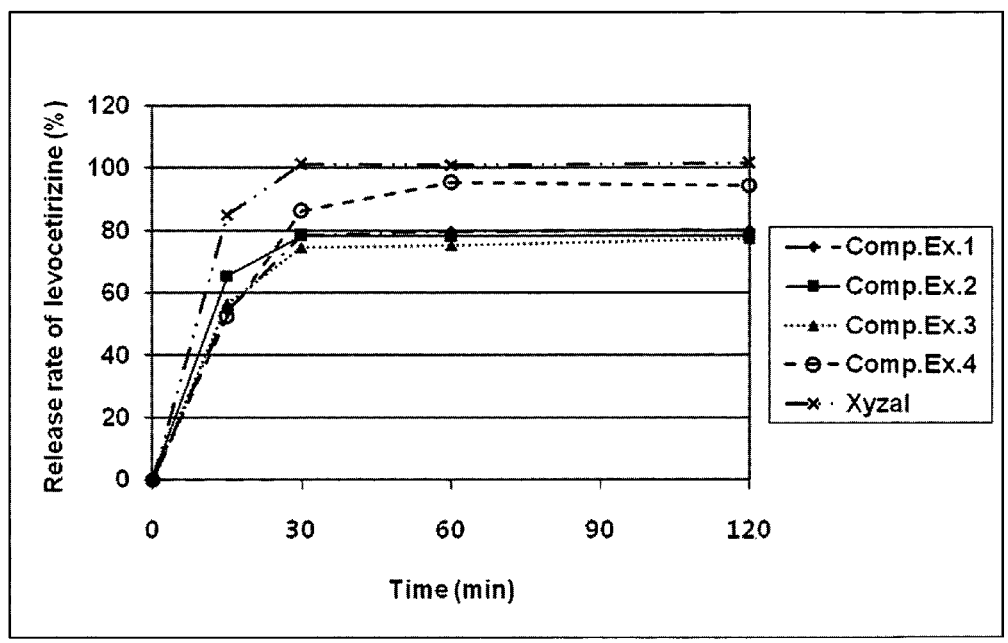
FIG. 4: the release rates of levocetirizine from the complex compositions obtained in Comparative Examples 1 to 4, and Xyzal.
Figure 5:
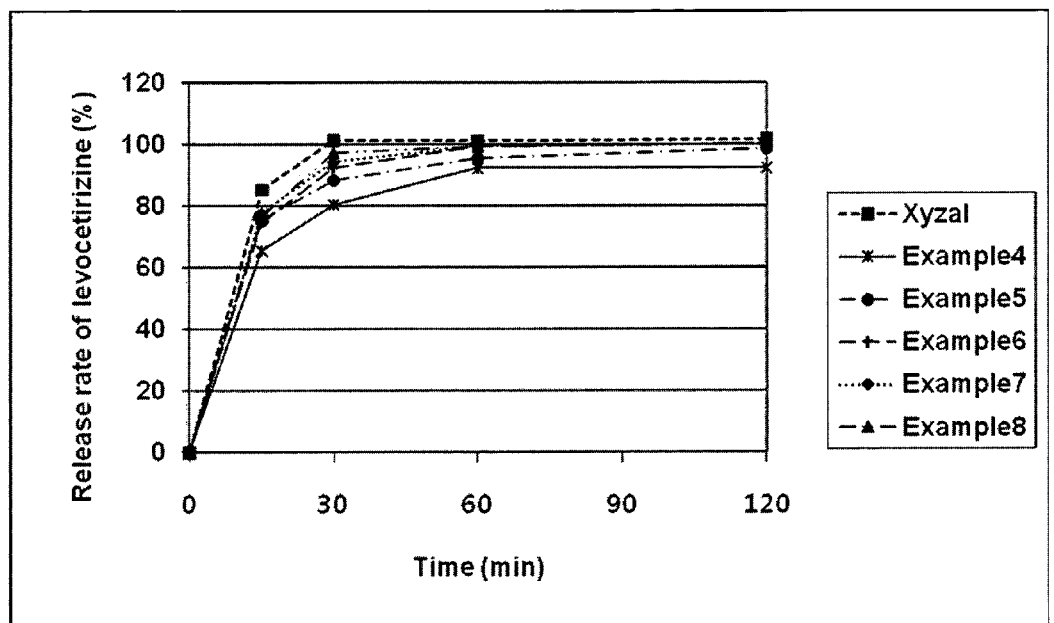
FIG. 5: the release rates of levocetirizine from the complex compositions obtained in Examples 4 to 8, and Xyzal.
Figure 6:
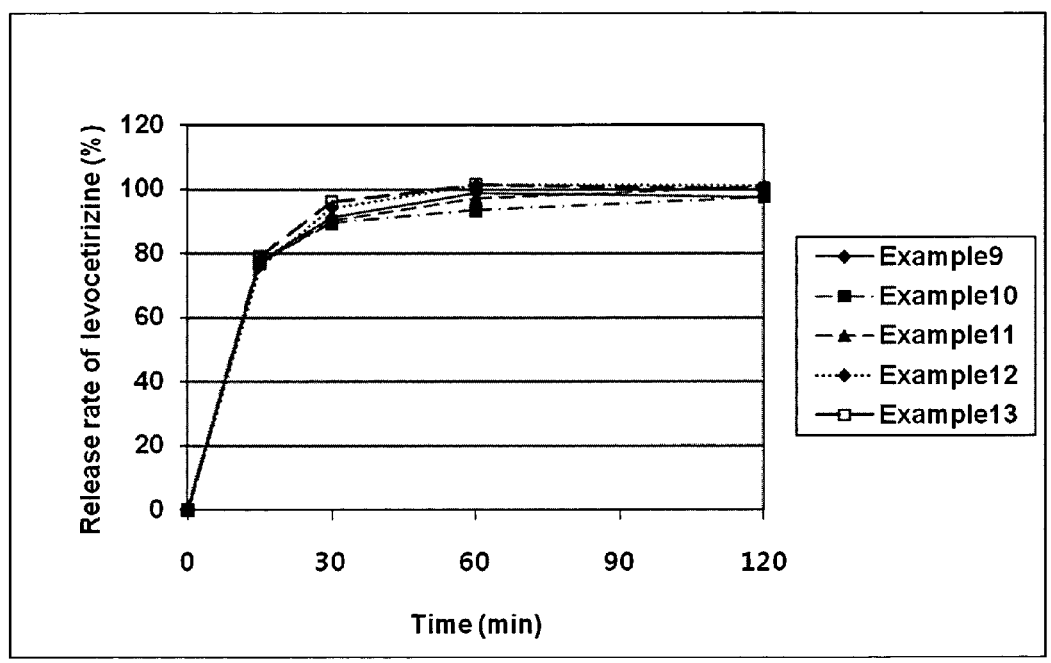
FIG. 6: the release rates of levocetirizine from the complex compositions obtained in Examples 9 to 13.
Figure 7:
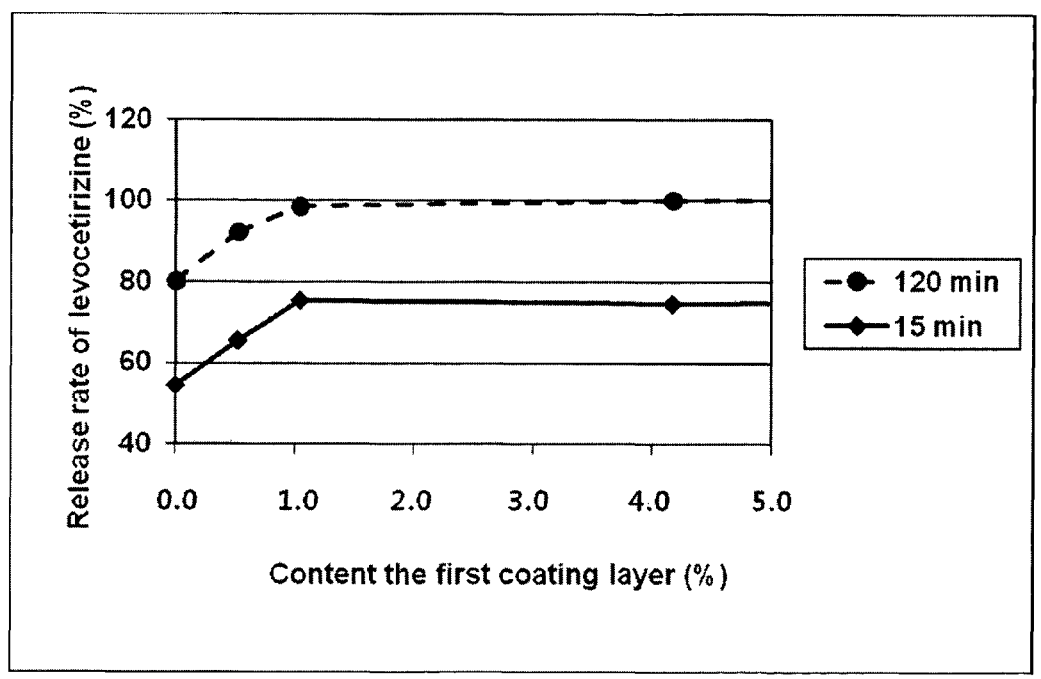
FIG. 7: the release rates of levocetirizine within 15 min and 120 min depending on the amount of the first coating layer in the complex compositions obtained in Comparative Example 1 and Examples 4 to 6.

As shown in FIG. 3, when the amount of the first coating layer is over 17 wt % based on the total weight of the core, the f2 decreased to 50 or less, which means a significance change. Accordingly, it is preferable that the amount of the first coating layer is 17 wt % or less based on the total weight of the core.

EXPERIMENTAL EXAMPLE 2

Releasing Test of Levocetirizine

The complex compositions obtained in Comparative Examples 1 to 4, and Example 4 to 13 were subjected to a releasing test in 900 ml of 0.1N HCl solution at a rate of 100 rpm according to the paddle method (releasing method type II described in the Korean pharmacopoeia). The effluent was collected at 15, 30, 60 and 120 min after releasing and the releasing rate of levocetirizine was calculated using the effluent. The results are shown in FIGS. 4 to 7 with the releasing test result of an immediate-release agent, Xyzal (UCB pharma).

As shown in FIGS. 4 to 7, the releases of the Comparative Examples 1 to 3 were delayed after 30 min. Such a result is caused that the hydrogel in the pseudoephedrine core absorbed water and swelled to inhibit the releasing behavior of levocetirizine from the levocetirizine coating layer. However, in Examples 4 to 13 in which an aqueous coating layer was formed between the pseudoephedrine core and the levocetirizine coating layer, the releasing rate of levocetirizine was enhanced. The Comparative Example 4 comprising hydroxypropylmethylcellulose as the second coating material also showed an enhanced releasing rate. From the result, it is found that the releasing rate of levocetirizine is not affected by the core when the amount of the first coating layer is 1 wt % or more based on the total weight of the core.

EXPERIMENTAL EXAMPLE 3

Change of Levocetirizine Releasing Rate for Accelerated Storage

The complex compositions obtained in Comparative Examples 1 to 4 and Examples 4 to 13 were placed in high-density polyethylene bottle and kept in the condition of 40° C. and a relative humidity of 75%. The samples were collected after 3 month and 6 month of test, and observed the releasing rate of levocetirizine in a same manner of Experimental Example 2. The results are shown in FIGS. 8 and 9 with the result of Xyzal.

Figure 8:
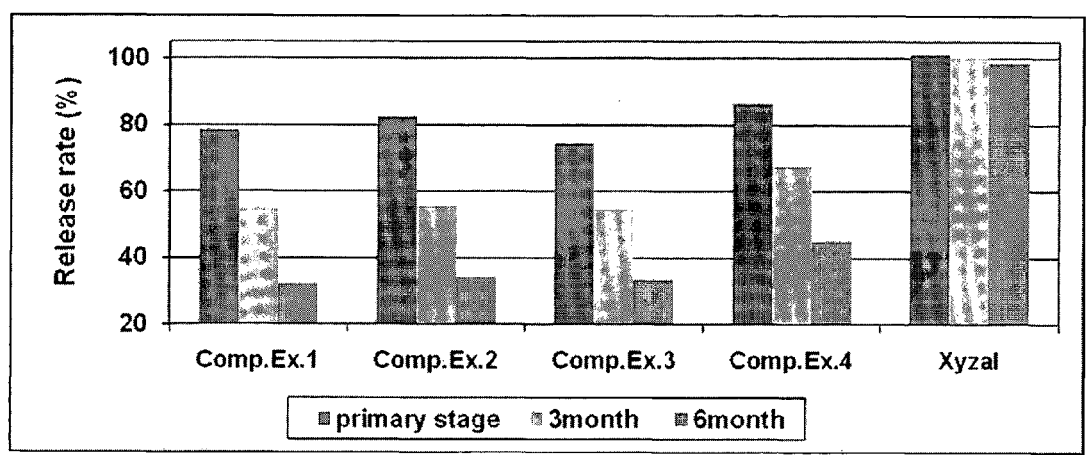
FIG. 8: the release rates of levocetirizine from the complex compositions obtained in Comparative Examples 1 to 4, and Xyzal for an accelerated storage time, 30 min.
Figure 9:
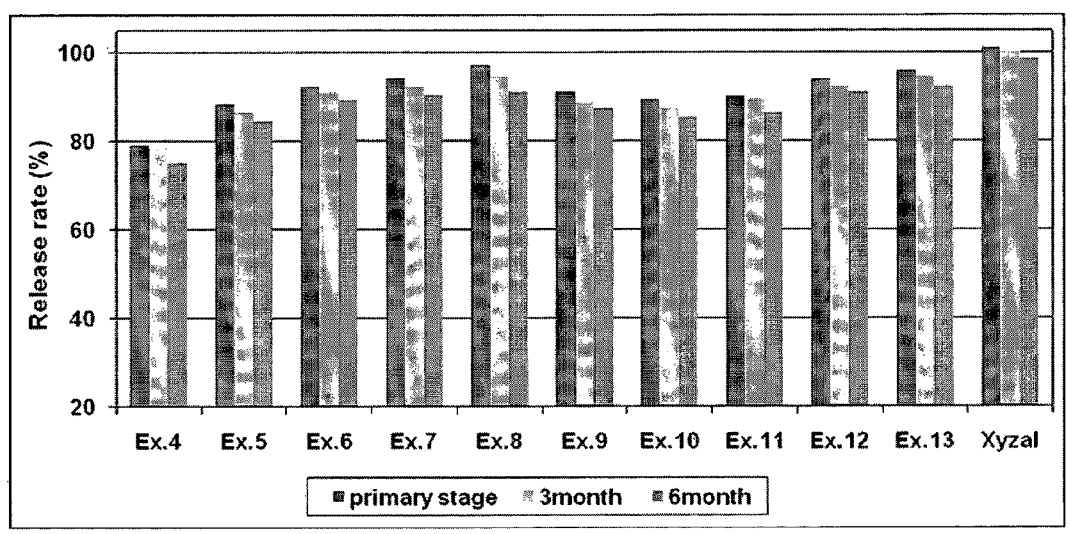
FIG. 9: the release rates of levocetirizine from the complex compositions obtained in Examples 4 to 13, and Xyzal for an accelerated storage time, 30 min.

As shown in FIGS. 8 and 9, all of Comparative Example 1 to 4 showed the deteriorated release rate in the condition of the a accelerated storage while all of Examples 4 to 13 showed stable releasing rate.

While the invention has been described with respect to the above specific embodiments, it should be recognized that various modifications and changes may be made to the invention by those skilled in the art which also fall within the scope of the invention as defined by the appended claims.

What is claimed is:

1. An oral composition comprising:
   (i) a core comprising a swellable hydrogel-forming agent and pseudoephedrine, or a pharmaceutically acceptable salt thereof;
   (ii) a water-soluble first coating layer which encases the core and comprises a water-soluble substance; and
   (iii) a second coating layer deposited on the first coating layer, which comprises levocetirizine or a pharmaceutically acceptable salt thereof together with polyvinylalcohol, povidone, polyvinylalcohol-polyethyleneglycol graft copolymer or a mixture thereof,
   wherein the swellable hydrogel-forming agent is selected from the group consisting of polyoxyethylene, hydroxypropylmethylcellulose, and xanthan gum, and the amount of the swellable hydrogel-forming agent is 0.1 to 10 weight part based on 1 weight part of pseudoephedrine;
   wherein the water-soluble substance is hydroxypropylmethylcellulose;
   wherein the first coating layer is formed from a water-acetone solution comprising the hydroxypropylmethylcellulose;
   wherein an amount of the first coating layer is 1 to 17 percent by weight based on the weight of the core and an amount of the second coating layer is 5 to 50 percent by weight part based on the core; ands
   wherein amounts of the polyvinylalcohol, povidone, polyvinylalcohol-polyethyleneglycol graft copolymer, or a mixture thereof are each of 10 to 100 weight part based on 1 weight part of levocetirizine.

2. The oral composition of claim 1, wherein the swellable hydrogel forming agent is polyoxyethylene.

3. The oral composition of claim 1, which further comprises a pharmaceutically acceptable additive.

4. The oral composition of claim 1, which shows a levocetirizine releasing rate of 80% or more in a 0.1 N HCl solution in 30 min.

5. An oral composition consisting of:
   (i) a core comprising a swellable hydrogel-forming agent and pseudoephedrine, or a pharmaceutically acceptable salt thereof;
   (ii) a water-soluble first coating layer which encases the core and comprises a water-soluble substance; and
   (iii) a second coating layer deposited on the first coating layer, which comprises levocetirizine or a pharmaceutically acceptable salt thereof together with polyvinylalcohol, povidone, polyvinylalcohol-polyethyleneglycol graft copolymer or a mixture thereof,
   wherein the swellable hydrogel-forming agent is selected from the group consisting of polyoxyethylene, hydroxypropylmethylcellulose, and xanthan gum, and the amount of the swellable hydrogel-forming agent is 0.1 to 10 weight part based on 1 weight part of pseudoephedrine;
   wherein the water-soluble substance is hydroxypropylmethylcellulose;
   wherein the first coating layer is formed from a water-acetone solution comprising the hydroxypropylmethylcellulose;
   wherein an amount of the first coating layer is 1 to 17 percent by weight based on the weight of the core and an amount of the second coating layer is 5 to 50 percent by weight part based on the core; and
   wherein amounts of the polyvinylalcohol, povidone, polyvinylalcohol-polyethyleneglycol graft copolymer, or a mixture thereof are each of 10 to 100 weight part based on 1 weight part of levocetirizine.

* * * * *